United States Patent [19]

Luetzow et al.

[11] 4,178,309

[45] Dec. 11, 1979

[54] MANUFACTURE OF SYMMETRICAL DIALKYLUREAS

[75] Inventors: Dietrich Luetzow, Limburgerhof; Norbert Neth, Bobenheim-Roxheim; Ulrich Wagner, Limburgerhof; Klaus Volkamer, Frankenthal, all of Fed. Rep. of Germany

[73] Assignee: BASF Aktiengesellschaft, Fed. Rep. of Germany

[21] Appl. No.: 930,160

[22] Filed: Aug. 2, 1978

[30] Foreign Application Priority Data

Aug. 5, 1977 [DE] Fed. Rep. of Germany ....... 2735265

[51] Int. Cl.$^2$ .................................... C07C 127/15
[52] U.S. Cl. ........................................ 260/553 R
[58] Field of Search ................... 260/553 R, 555 A

[56] References Cited

FOREIGN PATENT DOCUMENTS

| | | |
|---|---|---|
| 937586 | 12/1955 | Fed. Rep. of Germany. |
| 1768256 | 4/1974 | Fed. Rep. of Germany. |
| 750549 | 6/1956 | United Kingdom ............... 260/553 R |

OTHER PUBLICATIONS

Oriental Ind., CA 51:7671e (1956).
Etsuro et al., CA 52:18222cd (1958).
Michelitsch et al., CA 79:146024p (1973).

*Primary Examiner*—Thomas A. Waltz
*Attorney, Agent, or Firm*—Keil & Witherspoon

[57] ABSTRACT

A process for the manufacture of symmetrical dialkylureas by reacting monoalkylamines with $CO_2$ at an elevated temperature and under superatmospheric pressure, in which the unconverted starting materials, water and the by-products formed in the reaction zone, as well as alkylamine alkylcarbamate, after thermal decomposition into monoalkylamine, $CO_2$ and water, are separated from the dialkylurea formed, and thereafter a part of the unconverted starting materials plus by-products, with or without water, may or may not be recycled to the reaction zone, before isolating an aqueous solution, containing monoalkylamines, $CO_2$ and other by-products, which solution is treated with alkali metal hydroxide solution in a column, the monoalkylamine, after separation from carbon dioxide and water, being recycled to the reaction zone. The dialkylureas obtained contain not more than 1% of monoalkylurea and 1% of trialkylurea, and may be used as starting materials for various syntheses.

1 Claim, 1 Drawing Figure

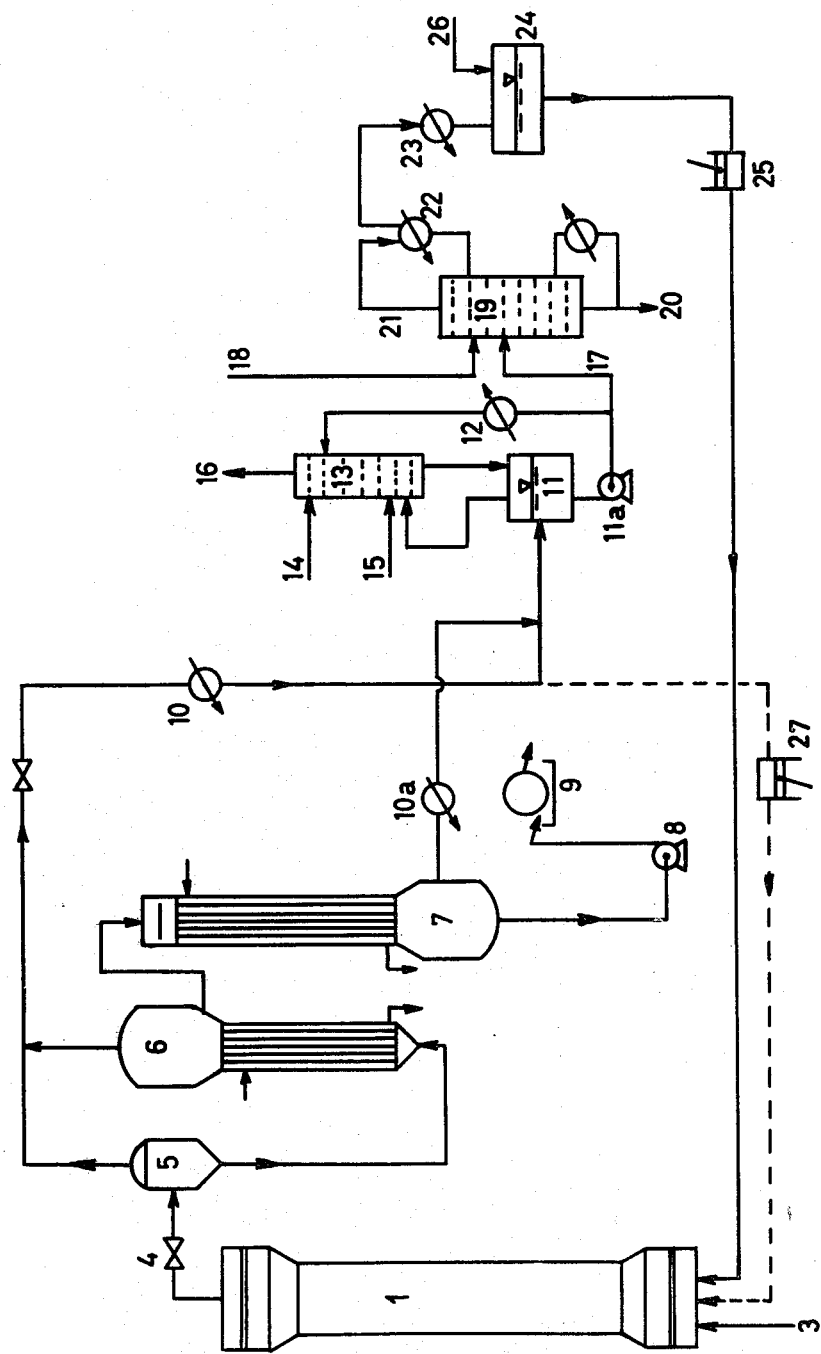

MANUFACTURE OF SYMMETRICAL DIALKYLUREAS

The present invention relates to a process for the manufacture of symmetrical dialkylureas, as set out in the claim.

The invention is based on a process as described in the preamble of the claim. German Pat. No. 937,586 discloses a method of preparing a symmetrical dialkylurea by reacting a monoalkylamine with carbon dioxide at an elevated temperature and under superatmospheric pressure. In this high pressure process, the reaction of monomethylamine with carbon dioxide only proceeds to about 60-75% conversion of the $CO_2$ employed; hence, the unconverted starting materials are removed from the reaction melt by letting down and heating, are taken up in water, whilst cooling, are again brought to the pressure at which the synthesis is carried out and are recycled to the reactor. This however introduces substantial amounts of water into the reaction zone, as a result of which the conversion of monoalkylamine and carbon dioxide to dialkylurea may fall to 25%.

For this reason, German Pat. No. 1,768,256 proposed freeing the unconverted starting materials from the water formed in the reaction and then re-using them for the reaction. This results in a simple and reliable procedure and in higher yields.

Because of the by-products formed in the reaction zone, e.g. $NH_3$, dialkylamine and trialkylamine, a dialkylurea prepared by one of the above processes contains about 3% of monoalkylurea and more than 2% of trialkylurea as impurities in the end product.

Dialkylureas are important starting materials for various syntheses. However, the users of dialkylureas, especially of dimethylurea, require that the content of monoalkylurea in the dialkylurea should be at most 1%, and that the content of trialkylurea should also be at most 1%.

It is true (cf. Comparative Example 2a) that if a certain loss of monoalkylamine is tolerated, the content of monoalkylurea can, under certain conditions, namely by removing a certain amount of monomethylamine/$NH_3$ mixture, be lowered to a value of about 1%. However, this leaves the trialkylurea content unchanged. It would appear obvious also to remove certain amounts of the other impurities, such as dialkylamine or trialkylamine, in addition to $NH_3$; however, this method is uneconomical since the entire amount of unconverted alkylamine to be recycled would have to be fractionated.

The process according to the invention, as defined in the characterizing clause of the claim, makes it possible to lower the content of both monoalkylurea and trialkylurea in the end product. Accordingly, purer products can be prepared by the process of the invention, and comparatively low losses of amine have to be tolerated. The process according to the invention is very flexible since it is possible to improve substantially on the specifications required by the users of the dialkylurea, if a certain loss of monoalkylamine is tolerated; on the other hand, it is possible to reduce this loss and still just achieve the permissible values of 1% of monoalkylurea and 1% of trialkylurea in the end product.

The starting materials used for the process according to the invention are monoalkylamines and carbon dioxide. The monoalkylamines are as a rule used in an amount of from 2 to 5 moles, especially from 2 to 3 moles, per mole of carbon dioxide. Preferred monoalkylamines are of 1 to 3 carbon atoms, examples being methylamine, ethylamine and n-propylamine. The conversions decrease in the above sequence; ie. with increasing atomic weight. For branched alkylamines, other processes of manufacture of the corresponding dialkylureas are to be preferred.

The process according to the invention will be illustrated below for the example of dimethylurea, to which the process is preferentially applied.

The reaction is in general carried out at from 150° to 220° C., preferably from 180° to 200° C., and at a pressure of from 30 to 160 bars, preferably from 100 to 150 bars. The process according to the invention may be carried out either continuously or batchwise, the former being preferred.

In addition to the above raw materials, the reaction zone may or may not be supplied additionally with a part of the carbamate condensed downstream from the decomposer, this carbamate constituting a 3rd component, and with recovered monomethylamine, constituting a 4th component.

The melt obtained in the high-pressure reactor contains dimethylurea, the water of reaction, unconverted starting materials, namely $CO_2$ and methylamine, the latter essentially in the form of alkylamine alkylcarbamate, and the by-products nitrogen, $NH_3$, dimethylamine and trimethylamine.

The unconverted starting materials and the by-products are as a rule separated from the dimethylurea by letting down the pressure, and heating the mixture; this decomposes the carbamate. The greater part of the water of reaction is removed by evaporation. The dimethylurea melt obtained after these operations is cooled and the end product is isolated therefrom in the conventional manner by crystallization, using cooling rollers. If the teaching of the invention is followed, the end product contains at most 1% of methylurea and 1% of trimethylurea as impurities.

The separation of the dimethylurea from the unconverted starting materials and the by-products is advantageously carried out as follows. The reaction melt is passed into a separator where it is let down from the reaction pressure to a pressure of about 2-10 bars. The molten mass then passes into the carbamate decomposer, where the carbamate is decomposed into methylamine and $CO_2$ at from 120° to 150° C. and within the above pressure range. The melt thereupon left is finally preferably freed from residual amounts of $CO_2$, methylamine and especially water in a reduced pressure falling film evaporator. The evaporator is preferably operated at from 100° to 120° C. and under a pressure of from 50 to 100 mm Hg.

The gases and vapors which leave the separator and to carbamate decomposer, and which contain methylamine, $CO_2$, ammonia, nitrogen, dimethylamine and trimethylamine, as well as water vapor, are combined and condensed after passing through a pressure-reducing valve. The entire amount, or the residual amount left after direct recycling of part of the carbamate to the reaction zone, is passed into a collecting vessel which is connected to a wash column which can be fed with water. The amine-containing vapors from the reduced pressure evaporator can also be fed to this collecting vessel. In this vessel, an aqueous solution forms, which as a rule contains from 15 to 35% by weight of methylamine and $CO_2$ in the form of their carbamate, together with $NH_3$, dimethylamine and trimethylamine. The temperature of the aqueous solution, both in the collecting vessel and in the wash column connected thereto is as a rule from 50° to 80° C., preferably from 55° to 70° C. The pressure in the equipment may be from 1.1 to 3 bars.

An inert gas, e.g. nitrogen, is introduced as the stripping agent into the bottom of the wash column; as a rule, from 2 to 40 cubic meters (S.T.P.) of stripping agent are required per 100 kg of dimethylurea. The aqueous solution present in the collecting vessel is fed by means of a pump to the top of the column. At the top of the column, a gas enriched with ammonia, dimethylamine and trimethylamine is taken off under the above conditions. The ratio of methylamine to $CO_2$ in the aqueous solution in the collecting vessel can be varied by adding $CO_2$ or methylamine to the stripping agent, and hence the ratio of $NH_3$ to dimethylamine in the off-gas of the column (ie. in the flare gas) can be controlled. Connecting the collecting vessel to the stripping column therefore makes it possible to remove a certain amount of undesired reaction by-products continuously from the aqueous solution, and thereby to control the purity of the end product.

The proportion of $NH_3$ in the column off-gas is the greater, the higher is the proportion of $CO_2$ in the aqueous solution; the converse is the case with the proportion of dimethylamine in the off-gas.

A certain amount of the aqueous solution is continuously fed from the collecting vessel to the treatment column; in this treatment column, the aqueous solution is separated into $CO_2$ and methylamine by treatment with a base.

This treatment is carried out with an alkali metal hydroxide solution, for example 10-25% strength by weight aqueous potassium hydroxide solution or, preferably, sodium hydroxide solution. The amount of alkali hydroxide used, based on the amount of carbon dioxide to be bonded, may vary from the stoichiometric amount to 1.1 times the stoichiometric amount. The treatment with the alkali metal hydroxide solution is carried out at from 80° to 130° C., preferably from 90° to 110° C., under a pressure of from 1 to 3 bars, advantageously using a column packed with Raschig rings, the liquid taken off the collecting vessel being passed into the middle part of the column. The alkali metal hydroxide solution is introduced at the top of the treatment column, trickles down through the column, and bonds the carbon dioxide of the aqueous carbamate solution originating from the collecting vessel; at the top of the column, the methylamine to be recycled is taken off. At the bottom of the column, an aqueous carbonate solution, which contains virtually the entire carbon dioxide, in a chemically bonded form, together with the water of reaction, is separated off. The temperature of the treatment column is in general kept constant by the thermal energy contained in the hot gases and liquid which enter the column; however, additional measures may be used if necessary, for example by heating the column with superheated system.

The methylamine leaving the top of the column is compressed, cooled, depending on the conditions, to from −20° to +30° C. (corresponding to a pressure of from 0.5 to 5 bars) and then passed in the liquid form into the tank, from where it can be recycled to the reaction zone by means of a pump.

The dialkylureas obtainable by the process of the invention, especially dimethylurea, are valuable starting materials for the preparation of pesticides, drugs and assistants for textile finishing and paper finishing.

The sequence of the process according to the invention will be explained in more detail below with the aid of the FIGURE:

From the reactor (1), the reaction melt first passes through a pressure reducing valve (4) into the separator (5). The liquid constituent is taken off the separator and introduced into the carbamate decomposer (6). From there, the melt, which has thereby been virtually substantially pre-purified, passes into the reduced pressure evaporator (7), from where the melt is pumped by means of the pump (8) to cooling rollers in which the end product is caused to solidify. It is obtained in the form of flakes.

The unconverted starting materials and the reaction by-products which leave the separator and the carbamate decomposer in the form of vapors are collected, liquefied, after passing through a pressure reducing valve, in the condenser (10) and collected in their entirety, or partially, in the collecting vessel (11). Part of the carbamate may or may not be directly fed into the reactor by means of a high pressure pump 27. The amine-containing vapors from the reduced pressure evaporator 7, which are condensed in the condenser 10a, can also be received in the collecting vessel. The said vessel is connected via a gas line to the stripper column (13); the liquid from the collecting vessel is fed to the top of the stripper column by means of a pump (11) via a heat exchanger (12). Water may be introduced at the top of the column through line (14), whilst the stripping agent (nitrogen, to which $CO_2$ or methylamine may or may not be admixed) enters the bottom of the column through line (15). Alternatively, $CO_2$ or methylamine may be introduced directly into the solution in the collecting vessel. A gas containing nitrogen, ammonia, methylamine, dimethylamine and trimethylamine is taken off through line (16) and is passed to the flare or is worked up in some other way. The aqueous solution from the collecting vessel passes through line (17) into the middle portion of the treatment column (19). Alkali metal hydroxide solution, especially sodium hydroxide solution, is introduced at the top of the column through line (18). At the bottom of the treatment column (19), alkali metal carbonate solution, in particular sodium carbonate solution, drains off through line (20). Methylamine gas is taken off through line (21), and is then compressed and cooled (23) and passed into the liquid methylamine supply tank (24), from where, after compression in the high pressure pump (25), it enters the reactor. Fresh amine is fed into the supply tank (24) through line (26). $CO_2$ is fed to the reactor through line (3).

The process according to the invention is illustrated in more detail in Examples 2b and c which follow, and which relate to the manufacture of dimethylurea. Comparative Example 1 shows that using the prior art process, ie. without removal of $NH_3$ from the system, an end product containing up to 3% of monomethylurea and up to 2.5% of dimethylurea can be obtained. If, as in Example 2a, only monomethylamine enriched with ammonia is removed from the system, a product containing about 1% of monomethylurea is obtained, the proportion of timethylurea remaining as high as before. However, if the process according to the invention is carried out, ie. with stripping by means of an inert gas, for example nitrogen, end products which conform to the required specifications, ie. which contain less than 1% of monomethylurea and less than 1% of trimethylurea, may be obtained.

COMPARATIVE EXAMPLE

1a. A reaction mixture from which 250 kg/hour of N,N'-dimethylurea can be obtained, the conversion of the reaction mixture being about 75% based on the amount of $CO_2$ employed, is formed, at 200° C. and 150 bars, in a reactor fed, per hour, with 400 kg of monomethylamine and 84 cubic meters (S.T.P.) of $CO_2$. The unconverted carbamate is decomposed by heating under reduced pressure, condensed together with the excess amine and the reaction by-products, combined with the vapors from the falling film evaporator and thereby dissolved in water, and treated with NaOH in a treatment column in order to bond the $CO_2$. In this way, 216 kg/hour of a gas mixture consisting in the main of monomethylamine, with up to 10% by weight of $NH_3$, dimethylamine and trimethylamine, can be recovered. The recovered amine mixture, together with fresh amine, is recycled to the reactor. This process gives an end product which still contains 2.8% by weight of monomethylurea and 2.2% by weight of trimethylurea as impurities.

1b. The procedure described above under 1a is followed except that half the products from the carbamate decomposer are directly recycled to the reaction zone, before combining the remainder with the vapors from the falling film evaporator. In this method, the end product obtained has exactly the same specification as that described in 1a.

EXAMPLE

2a. Comparative experiment (not prior art).

If, as described in Comparative Example 1a, the gas mixture obtained after the treatment with sodium hydroxide solution is only partially condensed, and 13 kg/hour of a gas mixture consisting of monomethylamine and 1.0 kg of ammonia is fed to the off-gas flare or employed for some other use, 250 kg/hour of dimethylurea are obtained, which now only contains 1% of monomethylurea, but still contains 2.2% by weight of trimethylurea as an impurity.

The loss of 7% by weight of monomethylamine, resulting from discharge from the system, must be compensated by adding a corresponding amount of fresh amine.

2b. Monomethylamine and $CO_2$ were reacted as described in Comparative Example 1a except that, in accordance with the invention, 500 l of a solution containing 25% by weight of amines and about 10% by weight of $CO_2$ were pumped at 60° C., as a recycling system, to the top of the stripping column, whilst at the bottom 12 cubic meters (S.T.P.)/hour of nitrogen were introduced as the stripping gas. Together with the stripping gas (nitrogen), 13 kg/hour of an amine mixture which contained, in addition to monomethylamine, 1.2 kg of ammonia, 1.3 kg of dimethylamine and 0.3 kg of trimethylamine, were fed to the flare. Per hour, 250 kg of dimethylurea which only contained 0.8% by weight of monomethylurea and 1% by weight of trimethylurea were obtained.

The loss of 7% by weight of monomethylamine, resulting from the discharge of material from the system, must be compensated by a corresponding addition of fresh amine.

2c. The procedure followed was as described under 2b above. However, the amount of gas used for stripping was 8 cubic meters (S.T.P.)/hour. This gave an end product containing 1% of monomethylurea and 1.2% by weight of trimethylurea. In this case, the loss of 5% by weight of monomethylamine had to be compensated by a correspondingly large addition of fresh amine.

2d. If, as described under 1b, 50% of the carbamate is directly fed to the reaction zone and in other respects the procedure described under 2b or 2c is followed, the losses of monomethylamine are the same as before, namely 7 and 5% by weight respectively, and the products obtained have specifications corresponding to those stated in Examples 2b and 2c respectively.

We claim:

1. A process for the manufacture of a symmetrical dialkylurea by reacting a monoalkylamine with $CO_2$ at an elevated temperature and under superatmospheric pressure, in which the unconverted starting materials, water and the by-products formed in the reaction zone, as well as alkylamine alkylcarbamate, after thermal decomposition into monoalkylamine, $CO_2$ and water, are separated from the dialkylurea formed, and thereafter a part of the unconverted starting materials plus reaction by-products, with or without water, may or may not be recycled to the reaction zone, before isolating an aqueous solution, containing a monoalkylamine, $CO_2$ and other reaction by-products, which solution is treated with alkali metal hydroxide solution in a column, the monoalkylamine, after separation from $CO_2$ and water, being recycled to the reaction zone, in which process the aqueous solution, before treatment with alkali metal hydroxide solution, is stripped, in a subsidiary column, with an inert gas to which $CO_2$ or monoalkylamine may or may not be admixed, and at least a part of the reaction by-products formed is taken off at the top of the column, the liquid discharged from the bottom of the subsidiary column is fed, via a collecting vessel, to the alkali treatment column, and the stream of gas issuing at the top of the treatment column is compressed without further purification and is liquefied by cooling.

* * * * *